United States Patent [19]

Matsumura et al.

[11]  4,190,656
[45]  Feb. 26, 1980

[54] URACIL DERIVATIVES AND PRODUCTION THEREOF

[75] Inventors: Koichi Matsumura, Ibaraki; Osamu Miyashita, Osaka; Hiroshi Shimadzu, Settsu; Naoto Hashimoto, Suita, all of Japan

[73] Assignee: Takeda Chemical Industries, Ltd., Osaka, Japan

[21] Appl. No.: 944,769

[22] Filed: Sep. 22, 1978

[30] Foreign Application Priority Data

Sep. 22, 1977 [JP]  Japan .............................. 52/114193

[51] Int. Cl.$^2$ ............................................ C07D 239/10
[52] U.S. Cl. .............................. 424/251; 260/566 AE; 542/416; 544/300; 544/301
[58] Field of Search ..................... 544/301, 300; 260/566 AE; 542/416; 424/251

[56] References Cited

U.S. PATENT DOCUMENTS

| | | | |
|---|---|---|---|
| 3,360,523 | 12/1967 | Loux ....................................... | 544/301 |
| 3,466,280 | 9/1969 | Loux ....................................... | 544/301 |
| 3,775,406 | 11/1973 | Trueb ..................................... | 542/416 |
| 3,954,758 | 5/1976 | Schuman et al. .................... | 260/260 |
| 3,954,759 | 5/1976 | Anderson et al. .................... | 260/260 |
| 3,987,045 | 10/1976 | Bock et al. ........................... | 544/300 |
| 4,017,626 | 4/1977 | Gauri ..................................... | 424/251 |
| 4,071,519 | 1/1978 | Ozaki et al. .......................... | 424/251 |
| 4,080,455 | 3/1978 | Yasumoto et al. .................... | 424/251 |
| 4,088,646 | 5/1978 | Ishida et al. .......................... | 424/251 |

FOREIGN PATENT DOCUMENTS

1006155  9/1965  United Kingdom .

OTHER PUBLICATIONS

Johnson et al., J. Am. Chem. Soc. 55 (1933), pp. 3871–3873.

*Primary Examiner*—Arthur P. Demers
*Attorney, Agent, or Firm*—Burgess, Ryan and Wayne

[57]  ABSTRACT

New compounds of the formula $$\underset{O}{\overset{HN_3}{\underset{H}{\overset{\parallel}{\underset{N_1}{\bigg\downarrow}}}}}\overset{O}{\underset{4}{\overset{\parallel}{\underset{6}{\bigg|}}}}\overset{F}{\underset{COOR_1}{\underset{O-N=C\underset{R_3'}{\overset{R_2}{\diagdown}}}{}}}$$

(wherein $R_1$ represents a lower alkyl group: and $$=C\underset{R_3'}{\overset{R_2}{\diagdown}}$$

represents an alkylidene radical in which at least one of $R_2$ and $R_3$ is a lower alkyl which may optionally be substituted by phenyl, phenyl or a 5- or 6-membered aromatic ring including S, N or O, and the remainder, if any, is hydrogen; or a cycloalkylidene radical of up to six carbon atoms, to which a benzene ring may optionally be fused).

These compounds are produced by reacting the corresponding 6-acyloxy compounds with a compound of the formula $$HO-N=C\underset{R_3'}{\overset{R_2}{\diagdown}}.$$

The new compounds have antiviral activity and are useful to prolong the life spans of tumor-bearing animals.

29 Claims, No Drawings

URACIL DERIVATIVES AND PRODUCTION THEREOF

This invention relates to novel fluorouracil derivatives.

More particularly, this invention relates to fluorouracil derivatives which have a fluorine atom and an ester group in the 5- position and an alkylidene- or cycloalkylideneaminooxy group in the 6-position of the uracil ring.

The fluorouracil derivatives according to this invention are useful compounds which prolong the life spans of tumorbearing animals and have antiviral activity.

It is an object of this invention to provide the fluorouracil derivatives and methods for producing thereof.

Other objects will be made clear from the description appearing hereinafter.

This invention is directed to a compound of the following formula:

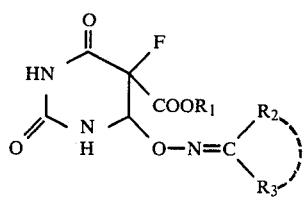
(I)

(wherein $R_1$ represents a lower alkyl group: and

represents an alkylidene radical in which at least one of $R_2$ and $R_3$ is a lower alkyl group which may optionally be substituted by phenyl, phenyl or a 5- or 6-membered aromatic ring including S, N or O, and the remainder, if any, is hydrogen; or
a cycloalkylidene radical of up to six carbon atoms, to which a benzene ring may optionally be fused).

The lower alkyl groups $R_1$, $R_2$ and $R_3$ may be the same or different and may for example be an alkyl group of up to 4 carbon atoms (e.g. methyl, ethyl, propyl, i-propyl, butyl, sec.-butyl, etc.). Further, the alkyl groups $R_2$ and $R_3$, respectively, may have more than 4 up to 6 carbon atoms (e.g. pentyl, i-pentyl, hexyl). $R_2$ and $R_3$, respectively as such an alkyl group, may be substituted by phenyl (e.g. benzyl or phenethyl). The 5- or 6-membered aromatic S-, N- and O-hetero rings as represented by $R_2$ or $R_3$, may, for example, be furyl, thienyl or pyridyl. As examples of the cycloalkylidene group of up to 6 carbon atoms as represented by

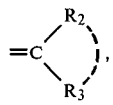

there may be mentioned cyclohexylidene, cyclopentylidene and cyclobutylidene, and a benzene ring may be fused to such a cycloalkylidene group to form for example indanylidene, benzocyclohexylidene or fluoroenylidene group.

The compound (I) according to this invention can be produced, for example by the following procedure.

Thus, it can be produced by reacting a compound of the formula:

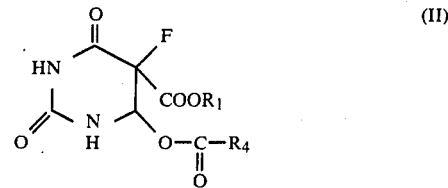
(II)

[$R_1$ is as defined hereinbefore: $R_4$—CO— is a carboxylic acid residue (acyl group)] with a compound of the formula:

(III)

($R_2$ and $R_3$ are respectively as defined hereinbefore)

As examples of $R_4$ there may be mentioned lower alkyls such as methyl and ethyl, mono-, di- and trihalogeno-lower alkyl groups (e.g. mono-, di- and trichloromethyl, trifluoromethyl) and phenyl.

Based on compound (II), compound (III) may be used in a suitable amount ranging from 1 to about 2 molar equivalents.

The reaction may be conducted at a suitable temperature from a temperature under ice-cooling to about 100° C.

This reaction may be carried out in a suitable solvent such as a ketone (e.g. acetone or methyl ethyl ketone), ester (e.g. ethyl acetate or butyl acetate), ether (e.g. tetrahydrofuran, dioxane or 1,2-dimethoxyethane) or dimethylformamide, or a suitable mixture of such solvents.

Sometimes this reaction is more advantageously conducted in the presence of a catalyst such as a tertiary amine (e.g. pyridine, picoline, triethylamine or dimethylaniline.)

The compound (I) produced in the above manner can be isolated and purified by conventional procedures such as concentration, solvent extraction, chromatography and recrystallization.

The compound (I) may occur in several stereo-isomers such as geometrical isomers and optical isomers due to the presence of asymmetrical carbon atoms at the 5- and 6-positions and the alkylideneaminooxy group. It is to be understood that all such individual isomers as well as their mixture are included in the scope of the present invention.

The compound (II) can be produced, for example by fluorinating a compound of the formula:

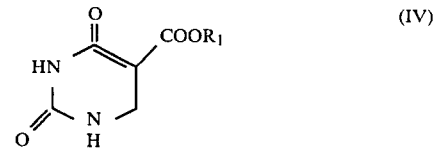
(IV)

($R_1$ is as defined hereinbefore) in the presence of $R_4$—COOH.

The fluorination may be carried out with a fluorinating agent. As examples of said fluorinating agent there may be mentioned fluorosulfur hypofluorites (e.g. pentafluorosulfur fluorite), lower fluoroalkyl hypofluorites containing 1 to 6 carbon atoms (e.g. trifluoromethyl hypofluorite, perfluoropropyl hypofluorite, perfluoroisopropyl hypofluorite, perfluoro-tert.-butyl hypofluorite, monochlorohexafluoropropyl hypofluorite and perfluoro-tert.-pentyl hypofluorite) and difluorooxy-compounds (e.g. 1,2 difluorooxydifluoroethane and difluorooxydifluoromethane). Molecular fluorine can likewise be employed. Where a gaseous fluorinating agent, molecular fluorine being an example, is employed, it is preferably bubbled through the reaction system after it has been diluted with an inert gas such as nitrogen or argon gas.

The fluorinating agent is desirably fluorine gas or trifluoromethyl hypofluorite. Based on compound (IV), the fluorinating agent may be used in a proportion of 1 to about 10 moles, preferably about 1.2 to 2.5 moles. The reaction temperature may be selected from the range of about −78° to +40° C., preferably about −20° C. to +30° C.

The compound (II) thus produced can be easily separated from the reaction mixture by procedures known per se. Desirably, for example, the solvent is evaporated under reduced pressure. The reaction mixture as such, without separation of compound (II), may be directly reacted with compound (III) to obtain compound (I).

The starting compound (II) may also be produced by the steps of fluorinating compound (IV) in the presence of water to prepare compound of the formula:

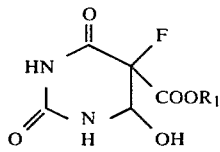

(V)

($R_1$ is as previously defined) and acylating (V) with an acylating agent which is a reactive derivative in the carboxyl function of $R_4$—COOH.

The fluorination reaction of compound (IV) in the presence of water can be conducted in the same manner as the aforementioned fluorination of compound (IV) in the presence of $R_4$—COOH. The acylation of compound (V) can be carried our by employing conventional procedures. For example, compound (V) may be acylated with a halide (e.g. chloride or bromide) or acid anhydride of the carboxylic acid $R_4$—COOH in the presence of an organic base (e.g. a tertiary amine such as pyridine, triethylamine, N-methylmorpholine or dimethylaniline.)

The compound (II) thus obtained need not necessarily be separated but the reaction mixture as such may be reacted with compound (III). Of course, (II) may be previously isolated by procedures known per se (e.g. removal of the solvent by distillation, recrystallization, chromatography, etc.)

The compounds (I) according to this invention effectively inhibit growth of tumorous cells, for example the cultured cell lines derived from various tumour cells such as KB-cells (cultured cells derived from human carcinoma of nasopharynx, C-34 cells (a cultured cell line of an in vitro virogenic mouse fibroblast tumour) and AC-cells (the astrocytoma cells of rat). Moreover, the compounds (I) display significant life-span-prolongation effects in mice with leukemia (P-388, L-1210). Thus, the compounds (I) according to this invention are of significant value. The compounds (I) according to this invention produce growth inhibition of various tumorous cells in mammals (e.g. rats, mice and human beings) and a life-span prolongation upon such mammals with leukemia.

The compounds (I) according to this invention may be administered alone or as formulated with pharmacologically acceptable carriers, excipients or diluents in the routine manner, e.g. in such dosage forms as powders, granules, dry syrups, tablets, capsules, suppositories, injections, etc., either orally or parenterally.

While the proper dosage depends on such factors as animal species, disease to be managed, condition and route of administration, in many cases it falls within the range of about 25 to 800 mg/kg body weight daily, the upper limit being usually about 400 mg/kg body weight and, more usually, about 200 mg/kg body weight, although there may be cases in which a deviation from the above range may prove beneficial.

Life-span prolongation in mouse leukemia L-1210

(1) Testing procedure $1 \times 10^5$ tumour cells were intraperitoneally transplanted into $BDF_1$ (C57BL/6×DBA/2) mice in groups of 5 animals and, at hour-24 and thereafter, the test drug was administered intraperitoneally or orally for 1 to 9 doses to determine their survival times in days. The results were expressed in the ratio of the median survival time in days of the treated animals (T) to the median survival time in days of the control animals (C)(T/C%).

(2) Test results

| Compound | Route of administration | Dosage (mg/kg day) | T/C (% life-span prolongation) |
|---|---|---|---|
| Ethyl 5-fluoro-6-cyclohexylidene-aminooxy-1,2,3,4, 5,6-hexahydro-2,4-dioxopyrimidine-5-carboxylate | Oral | 200 | 157 |
| | Oral | 100 | 134 |
| | Intraperitoneal | 200 | 114 |
| | Intraperitoneal | 100 | 161 |

EXAMPLE 1

In 6 ml. of acetone was dissolved 4.12 g. (20 m moles) of methyl 5-fluoro-6-hydroxy-1,2,3,4,5,6-hexahydro-2,4-dioxopyrimidine-5-carboxylate, and under ice-cooling, 2.55 g. (25 m moles) of acetic anhydride and 10 ml. of pyridine were added. The reaction was carried out with stirring overnight at room temperature. To the reaction mixture was added 2.26 g. (20 m moles) of cyclohexanone oxime. The mixture was stirred at room temperature for 2 hours, after which the reaction was conducted at 65° C. for 3 hours. The reaction mixture was concentrated to dryness under reduced pressure and the residue was subjected to silica gel column chromatography (developing solvent system; chloroform-/acetone=85/15, V/V). By the above procedure was obtained 4.0 g. of methyl 5-fluoro-6-cyclohexylideneaminooxy-1,2,3,4,5,6-hexahydro-2,4-dioxopyrimidine-5-carboxylate. m.p. 171°–175° C.(decomp.) (as recrystallized from acetone-chloroform-hexane) NMR(DMSO-$d_6$) δ0 1.66(6H, broad singlet), 1.9–2.6(4H, broad two peaks), 3.82(3H, s), 5.38(1H, dxd; after addition of $D_2O$, d, J=1Hz), 8.97(1H, broad), 11.07 (1H, broad)

Elemental analysis, for $C_{12}H_{16}FN_3O_5$: Calcd. C, 47.84; H, 5.35; N, 13.95: Found C, 47.82; H, 5.37; N, 13.87.

EXAMPLE 2

In 10 ml. of acetone was dissolved 8.80 g. (40 m moles) of ethyl 5-fluoro-6-hydroxy-1,2,3,4,5,6-hexahydro-2,4-dioxopyrimidine-5-carboxylate, and under ice-cooling, 5.10 g. (50 m moles) of acetic anhydride and 10 ml. of pyridine were added. The mixture was reacted at room temperature overnight. (A sample of the reaction mixture was taken, the solvent was distilled off under reduced pressure and the NMR spectrum of the residue was measured to ensure that there had been produced ethyl 6-acetoxy-5-fluoro-1,2,3,4,5,6-hexahydro-2,4-dioxopyrimidine-5-carboxylate.

NMR spectrum (DMSO-$d_6$) δ: (in addition to the peaks assignable to the remaining acetic acid, pyridine, etc.) 1.24(3H, t, J=7Hz), 1.93(3H, s), 4.33(2H, q, J=7Hz), 6.28(1H, q, slightly broad), 9.19(1H, broad), 11.04(- 1H, broad)).

To this reaction mixture was added 4.52 g. (40 m moles) of cyclohexanone oxime together with 10 ml. of pyridine. The mixture was heated at 60° C. for one hour. The reaction mixture was concentrated under reduced pressure and the residue was subjected to silica gel column chromatography (developing solvent system; chloroform/acetone=87.5/12.5, V/V).

By the above procedure there was obtained ethyl 5-fluoro-6-cyclohexylideneaminooxy-1,2,3,4,5,6-hexahydro-2,4-dioxopyrimidine-5-carboxylate. m.p. 185°-187° C.(decomp.) (recrystallized from acetone - chloroform - hexane).

NMR (DMSO-$d_6$) δ : 1.25(3H, t, J=7Hz), 1.56(6H, broad singlet), 1.9–2.6(4H, broad two peaks), 4.32(2H, q, J=7Hz), 5.43(1H, d×d, $J_{HF}$=1Hz, $J_{HH}$=5Hz), 8.98(1H, broad), 11.07(1H, broad).

Elemental analysis, for $C_{13}H_{18}FN_3O_5$: Calcd. C, 49.52; H, 4.75; N, 13.33: Found C, 49.61; H, 5.69; N, 13.31.

EXAMPLE 3

The procedure of Example 2 was repeated except that 9.04 g. (80 mmoles) of cyclohexanone oxime was used in lieu of 4.52 g. (40 mmoles) of the same reagent. By this procedure was obtained 10.5 g. of ethyl 5-fluoro-6-cyclohexylideneaminooxy-1,2,3,4,5,6-hexahydro-2,4-dioxopyrimidine-5-carboxylate.

EXAMPLE 4

A solution prepared from 8.80 g. (40 mmoles) of ethyl 5-fluoro-6-hydroxy-1,2,3,4,5,6-hexahydro-2,4-dioxopyrimidine-5-carboxylate, 5.10 g. (50 mmoles) of acetic anhydride 20 ml. of pyridine and 10 ml. of acetone was allowed to stand at room temperature overnight. Then, following addition of 4.38 g. (60 moles) of acetoxime, the mixture was reacted at 50°-60° C. for 3 hours. The reaction mixture was purified by a procedure similar to that described in Example 1. By the above procedure there was obtained 7.40 g. of ethyl 5-fluoro-6-isopropylideneaminooxy-1,2,3,4,5,6-hexahydro-2,4-dioxopyrimidine-5-carboxylate. m.p. 173°-178° C.(decomp.)(recrystallized from acetone - chloroform - hexane)

NMR (DMSO-$d_6$) δ: 1.20(3H, t, J=7Hz), 1.75(3H, s), 1.77 (3H, s), 4.28(2H, q, J=7Hz), 5.42(1H, d×d, $J_{HF}$=1Hz, $J_{HH}$=5Hz), 8.92(1H, broad), 11.02(1H, broad).

Elemental analysis, for $C_{10}H_{14}FN_3O_5$: Calcd. C, 43.64; H, 5.13; N, 15.27; Found C, 43.63; H, 5.09; N, 15.21.

EXAMPLE 5

A solution prepared from 6.60 g. (30 mmoles) of ethyl 5-fluoro-6-hydroxy-1,2,3,4,5,6-hexahydro-2,4-dioxopyrimidine-5-carboxylate, 3.27 g. (32 mmoles) of acetic anhydride, 10 ml. of pyridine and 10 ml. of acetone was allowed to stand at room temperature overnight. Then, following addition of 5.22 g. (35 mmoles) of phenylacetoxime, the mixture was heated at 50°-60° C. for 2 hours. The reaction product was purified by a procedure similar to that described in Example 1. By the above procedure was obtained 7.02 g. of ethyl 5-fluoro-6-phenylisopropylideneaminooxy-1,2,3,4,5,6-hexahydro-2,4-dioxopyrimidine-5-carboxylate. m.p. 135°-139° C. (recrystallized from acetone - chloroform - hexane).

NMR (DMSO-$d_6$) δ: 1.23(3H, t, J=7 Hz), 1.67(3H, s), 3.37(2H, s), 4.30(2H, q, J=7 Hz), 5.50(1H, d×d, $J_{HF}$=0.5 Hz, $J_{HH}$=5 Hz), 9.03(1H, broad), 11.15(1H, broad).

Elemental analysis, for $C_{16}H_{18}FN_3O_5$: Calcd. C, 54.70; H, 5.16; N, 11.96; Found C, 54.54; H, 4.95; N, 11.86.

EXAMPLE 6

A solution prepared from 6.60 g. (30 mmoles) of ethyl 5-fluoro-6-hydroxy-1,2,3,4,5,6-hexahydro-2,4-dioxopyrimidine-5-carboxylate, 3.27 g. (32 mmoles) of acetic anhydride, 10 ml. of pyridine and 10 ml. of acetone was allowed to stand at room temperature overnight. Then, 7.40 g. (35 mmoles) of benzyl phenyl ketoxime was added and the mixture was reacted at 60° C. for 3 hours. The reaction mixture was purified in the same manner as Example 1. By the above procedure there was obtained 7.40 g. of ethyl 5-fluoro-6-(α,β-diphenyl)ethylideneaminooxy-1,2,3,4,5,6-hexahydro-2,4-dioxopyrimidine-5-carboxylate. m.p. 173°-175° C. (recrystallized from acetone - chloroform).

NMR (DMSO-$d_6$) δ: 1.22(3H, t, J=7 Hz), 4.15(2H, s), 4.30(2H, q, J=7 Hz), 5.76(1H, ca. d, J=5 Hz), 9.08(1H, broad), 11.20(1H, broad).

Elemental analysis, for $C_{21}H_{20}FN_3O_5$: Calcd. C, 61.01; H, 4.88; N, 10.16; Found C, 60.90; H, 4.70; N, 10.03.

EXAMPLE 7

A solution prepared from 6.60 g. (30 mmoles) of ethyl 5-fluoro-6-hydroxy-1,2,3,4,5,6-hexahydro-2,4-dioxopyrimidine-5-carboxylate, 3.27 g. (32 mmoles) of acetic anhydrate, 10 ml. of pyridine and 10 ml. of acetone was allowed to stand at room temperature overnight. Then, 5.15 g. (35 mmoles) of 1-indanone oxime was added and the mixture was reacted at 60° C. for 3 hours. The reaction mixture was purified in the same manner as Example 1. By the above procedure there was obtained 3.38 g. of ethyl 5-fluoro-6-(1-indanylidene)aminooxy-1,2,3,4,5,6-hexahydro-2,4-dioxopyrimidine-5-carboxylate. m.p. 190°-193° C. (decomp.) (recrystallized from acetone - chloroform - hexane).

NMR (DMSO-$d_6$) δ: 1.23(3H, t, J=7 Hz), 2.56–3.10(4H, broad m), 4.30(2H, q, J=7 Hz), 5.57(1H, d×d, $J_{HF}$=0.5 Hz, $J_{HH}$=5 Hz), 7.40(4H, broad), 9.00(1H, broad), 11.10 (1H, broad).

Elemental analysis, for $C_{16}H_{16}FN_3O_5 \cdot H_2O$: Calcd. C, 52.32; H, 4.94; N, 11.44; Found C, 52.70; H, 4.34; N, 11.33.

EXAMPLE 8

A solution prepared from 8.80 g. (40 mmoles) of ethyl 5-fluoro-6-hydroxy-1,2,3,4,5,6-hexahydro-2,4-dioxopyrimidine-5-carboxylate, 4.60 g. (45 mmoles) of acetic anhydride, 10 ml. of pyridine and 10 ml. of acetone was allowed to stand at room temperature overnight. Then, 8.46 g. (60 mmoles) of methyl 2-thienyl ketoxime was added and the mixture was reacted at 60° C. for 3 hours. The reaction mixture was concentrated to dryness under reduced pressure and the residue was purified as in Example 1. By the above procedure was obtained 6.68 g. of ethyl 5-fluoro-6-(α-2-thienyl)ethylideneaminooxy-1,2,3,4,5,6-hexahydro-2,4-dioxopyrimidine-5-carboxylate. m.p. 201°–204° C. (decomp.) (recrystallized from acetone-chloroform - hexane).

NMR (DMSO-$d_6$) δ: 1.20(3H, t, J=7 Hz), 2.20(3H, s), 4.31(2H, q, J=7 Hz), 5.62(1H, d, J=5 Hz; after addition of $D_2O$, s), 7.0–7.8 (3H, m), 9.00(1H, broad), 11.17(1H, broad).

Elemental analysis, for $C_{13}H_{14}FN_3O_5S$: Calcd. C, 45.48; H, 4.11; N, 12.24; Found C, 45.33; H, 4.04; N, 12.22.

EXAMPLE 9

A solution prepared from 4.62 g. (21 mmoles) of ethyl 5-fluoro-6-hydroxy-1,2,3,4,5,6-hexahydro-2,4-dioxopyrimidine-5-carboxylate, 2.25 g. of acetic anhydride, 10 ml. of pyridine and 10 ml. of acetone was allowed to stand at room temperature overnight. Then, 3.3 g. (24.2 mmoles) of methyl 4-pyridyl ketoxime was added and the mixture was reacted on a water bath at about 90° C. for 3 hours.

The reaction mixture was concentrated to dryness under reduced pressure and the residue was purified as in Example 1. By the above procedure there was obtained 6.1 g. of ethyl 5-fluoro-6-(α-4-pyridyl)ethylideneaminooxy-1,2,3,4,5,6-hexahydro-2,4-dioxopyrimidine-5-carboxylate.

NMR (DMSO-$d_6$) δ: 1.20(3H, t, J=7 Hz), 2.16(3H, s), 4.30(2H, q, J=7 Hz), 5.75(1H, d×d, $J_{HF}$=0.5 Hz, $J_{HH}$=5 Hz), 7.50–8.55 (4H, m), 9.10(1H, broad), 11.27(1H, broad).

EXAMPLE 10

In a mixture of 12.5 ml. pyridine and 6.5 ml. acetone was dissolved 5.5 g. of ethyl 5-fluoro-6-hydroxy-1,2,3,4,5,6-hexahydro-2,4-dioxopyrimidine-5-carboxylate and, with the addition of 3.2 g. of acetic anhydride, the solution was stirred at room temperature overnight.

Then, 3.9 g. of benzaldoxime and 6.5 ml. of pyridine were added and the mixture was reacted at room temperature for one hour and at 50° C. for 2 hours. Thereafter, the reaction mixture was concentrated and dissolved in about 100 ml. of ethyl acetate. The solution was washed with water, dried and concentrated to dryness, whereupon a pale-orange oil was obtained. This oily product was subjected to silica gel column chromatography (developing solvent; benzene/acetone=10/1, V/V). By the above procedure there was obtained 2.1 g. of ethyl 5-fluoro-6-benzylideneaminooxy-1,2,3,4,5,6-hexahydro-2,4-dioxopyrimidine-5-carboxylate as white crystalline powders. m.p. 198°–199° C. (decomp.).

NMR spectrum (DMSO-$d_6$) δ: 1.24(3H, t, J=7 Hz), 4.34(2H, qua., J=7 Hz), 5.64(1H, d×d, J=1 Hz, 4 Hz), 7.36–7.80 (5H, m), 8.40(1H, s), 9.03(1H, broad), 11.15(1H, broad).

Elemental analysis, for $C_{14}H_{14}FN_3O_5$: Calcd. C, 52.02; H, 4.37; N, 13.00; Found C, 52.18; H, 4.21; N, 13.12.

EXAMPLE 11

In 200 ml. of acetic acid was dissolved 1.84 g. (10 mmoles) of ethyl 1,2,3,4-tetrahydro-2,4-dioxopyrimidine-5-carboxylate and a mixed gas of 15% fluorine - nitrogen (V/V) was bubbled through the solution at a temperature of 20°–25° C. After 1.5 molar equivalents of fluorine had been introduced, the solution was stirred at that temperature for an additional hour. The acetic acid was distilled off under reduced pressure and the residual solvent was further evaporated in vacuo to obtain 3.0 g. of crude ethyl 5-fluoro-6-acetoxy-1,2,3,4,5,6-tetrahydro-2,4-dioxopyrimidine-5-carboxylate as a viscous oil.

NMR spectrum (DMSO-$d_6$) δ: (in addition to peaks assignable to acetic acid) 1.24(3H, t, J=7 Hz), 2.11(3H, s), 4.35(2H, q, J=7 Hz), 6.21(1H, d×d, J=5.5 Hz & 2 Hz; after addition of $D_2O$, d, J=2 Hz), 9.13(1H, broad), 11.3(1H, broad).

The above oil was dissolved in a small amount of acetone and a solution of 2.26 g. (20 mmoles) of cyclohexanone oxime in 5 ml. of pyridine was added. The mixture was stirred at room temperature for one hour and heated at 60° C. for another hour. The reaction mixture was concentrated under reduced pressure and the residue was chromatographed as in Example 2. By the above procedure there was obtained 2.6 g. of ethyl 5-fluoro-6-cyclohexylideneaminooxy-1,2,3,4,5,6-hexahydro-2,4-dioxopyrimidine-5-carboxylate.

The following compounds (I) can be produced in the same manner as described hereinbefore and by the procedures set forth in the preceding examples.

Ethyl 5-fluoro-6-isobutylideneaminooxy-1,2,3,4,5,6-hexahydro-2,4-dioxopyrimidine-5-carboxylate;

Ethyl 5-fluoro-6-(α-methyl)butylideneaminooxy-1,2,3,4,5,6-hexahydro-2,4-dioxopyrimidine-5-carboxylate;

Ethyl 5-fluoro-6-(α-methyl)propylideneaminooxy-1,2,3,4,5,6-hexahydro-2,4-dioxopyrimidine-5-carboxylate;

Ethyl 5-fluoro-6-(α-methyl)pentylideneaminooxy-1,2,3,4,5,6-hexahydro-2,4-diocopyrimidine-5-carboxylate;

EXAMPLE 12

Ethyl 5-fluoro-6-hydroxy-1,2,3,4,5,6-hexahydro-2,4-dioxopyrimidine-5-carboxylate (6.60 g., 30 mmoles), acetic anhydride (3.27 g., 32 mmoles), pyridine (10 ml.) and acetone (10 ml.) were mixed and allowed to stand overnight at ordinary temperature (18°–23° C.). To this mixture were added cyclobutanone oxime (3.82 g., 45 mmoles) and pyridine (5 ml.) which was heated at 60° C. for 2 hours. Then, volatiles were removed under reduced pressure and the remaining mass was chromatographed on a column of silica gel with chloroform/acetone=85/15(V/V) to give 4.78 g of ethyl 5-fluoro-6-cyclobutylideneaminooxy-1,2,3,4,5,6-hexahydro-2,4-dioxopyrimidine-5-carboxylate.

m.p. 188°–189° C. (recrystallized from acetone - chloroform - hexane).

NMR spectrum (in DMSO-d$_6$) δ: 1.18(3H, t, J=7 Hz), 1.7–2.3 (2H, m), 2.5–3.1(4H, m), 4.25(2H, q, J=7 Hz), 5.32(1H, d×d, J=1 Hz and 5 Hz; after addition of D$_2$O, d, J=1 Hz), 8.90(1H, broad), 11.00(1H, broad).

Elemental analysis for C$_{11}$H$_{14}$FN$_3$O$_5$: Calcd. C, 46.00; H, 4.91; N, 14.63; Found C, 45.85; H, 4.80; N, 14.85.

EXAMPLE 13

By a procedure similar to that of Example 2 or 12, the following compounds were prepared from the corresponding starting materials.

(a) Ethyl 5-fluoro-6-cyclopentylideneaminooxy-1,2,3,4,5,6-hexahydro-2,4-dioxopyrimidine-5-carboxylate.

m.p. 170°–171° C. (recrystallized from acetone - chloroform - hexane).

NMR-spectrum (in DMSO-d$_6$) δ: 1.20(3H, t, J=7 Hz), 1.5–2.1 (4H, m), 2.1–2.7(4H, m), 4.27(2H, q, J=7 Hz), 5.36(1H, d×d, J=5 Hz and 1 Hz, after addition of D$_2$O, d, J=1 Hz), 8.90(1H, broad), 11.00(1H, broad).

Elemental analysis: Calcd. for C$_{12}$H$_{16}$FN$_3$O$_5$: C, 47.85; H, 5.35; N, 13.95; Found C, 47.72; H, 5.18; N, 14.06.

(b) Ethyl 5-fluoro-6-[α-(2-furyl)ethylidene]aminooxy-1,2,3,4,5,6-hexahydro-2,4-dioxopyrimidine-5-carboxylate.

m.p. 196°–197° C. (recrystallized from acetone - chloroform - hexane).

NMR-spectrum (in DMSO-d$_6$) δ: 1.22(3H, t, J=7 Hz), 2.06(3H, s), 4.30(2H, q, J=7 Hz), 5.60(1H, d×d, J=1 Hz and 5 Hz; after addition of D$_2$O, d, J=1 Hz), 6.57(1H, d×d, J=1 Hz and 3 Hz), 6.82(1H, d, J=3 Hz), 7.77(1H, d, J=1 Hz), 9.07(1H, broad), 11.13(1H, broad).

Elemental analysis: Calcd. for C$_{13}$H$_{14}$FN$_3$O$_6$: C, 47.71; H, 4.31; N, 12.84; Found C, 47.54; H, 4.15; N, 12.91.

(c) Ethyl 6-ethylideneaminooxy-5-fluoro-1,2,3,4,5,6-hexahydro-2,4-dioxopyrimidine-5-carboxylate (A mixture of almost equal amount of E and Z isomers).

m.p. 128°–129° C.

NMR-spectrum (in DMSO-d$_6$) δ: 1.18(3H, t, J=7 Hz), 1.70 and 1.73(total 3H, d+d, J=5.5 Hz), 4.28(2H, q, J=7 Hz), 5.41(1H, m), 7.01 and 7.52(total 1H, q+q, J=5 Hz), 8.93(1H, broad), 11.02(1H, broad).

Elemental analysis: calcd. for C$_9$H$_{12}$FN$_3$O$_5$: C, 41.38; H, 4.63; N, 16.09; Found, C, 41.38; H, 4.57; N, 16.08.

(d) Ethyl 5-fluoro-6-α,α-diphenylmethylilideneaminooxy-1,2,3,4,5,6-hexahydro-2,4-dioxopyrimidine-5-carboxylate m.p. 184°–185° C.

NMR spectrum (in DMSO-d$_6$) δ: 1.22(3H, t, J=7 Hz), 4.28(2H, q, J=7 Hz), 5.58(1H, d, J=4.5 Hz), 7.33(10H, broad), 9.35(1H, broad), 11.53(1H, broad).

Elemental analysis: calcd. for C$_{20}$H$_{18}$FN$_3$O$_5$: C, 60.15; H, 4.54; N, 10.52.; Found, C, 60.00; H, 4.43; N, 10.63.

(e) Ethyl 5-fluoro-6-α,α-diisobutylmethylideneaminooxy-1,2,3,4,5,6-hexahydro-2,4-dioxopyrimidine-5-carboxylate m.p. 145°–146° C.

NMR-spectrum (in DMSO-d$_6$) δ: 0.83(12H, broad d, J=5 Hz), 1.24(3H, t, J=7 Hz), 1.67–2.0(6H, m), 4.28(2H, q, J=7 Hz), 5.38(1H, d×d, J=4.5 Hz and 1 Hz), 8.83(1H, broad), 10.97(1H, broad).

Elemental analysis; calcd. for C$_{16}$H$_{26}$FN$_3$O$_5$: C, 53.47; H, 7.29; N, 11.69; Found, C, 53.61; H, 7.39; N, 11.47.

(f) Ethyl 5-fluoro-6-(E)-hexylideneaminooxy-1,2,3,4,5,6-hexahydro-2,4-dioxopyrimidine-5-carboxylate m.p. 128°–129° C.

NMR-spectrum (in DMSO-d$_6$) δ: 0.6–1.75(12H, m), 1.83–2.38 (2H, m), 4.26(2H, q, J=7 Hz), 5.34(1H, d×d, J=5 Hz and 1 Hz), 7.46(1H, t, J=5.5 Hz), 8.83(1H, broad), 10.75 (1H, broad).

Elemental analysis; Calcd. for C$_{13}$H$_{20}$FN$_2$O$_5$, C, 49.21; H, 6.35; N, 13.24; Found, C, 49.17; H, 6.37; N, 13.23.

(g) Ethyl 5-fluoro-6-(Z)-hexylideneaminooxy-1,2,3,4,5,6-hexahydro-2,4-dioxopyrimidine-5-carboxylate.

NMR-spectrum (in DMSO-d$_6$) δ: almost superimposable with that of the E-isomer, except for that the signal at δ 7.46(1H, t) in case of the latter compound is displaced to δ 6.89(1H, t, J=5.5 Hz).

EXAMPLE 14

To a suspension of 5.0 g. of ethyl 1,2,3,4-tetrahydro-2,4-dioxopyrimidine-5-carboxylate in 100 ml. of acetic acid, a gaseous mixture of fluorine/nitrogen=1/3(V/V) was passed with efficient stirring at ca. 18°–25° C., until UV-absorption at 270 nm due to the starting pyrimidine vanished. About 1.55 molar equivalent of fluorine was consumed. Then, the solvent was split off under reduced pressure to give a white solid, which was triturated with toluene and collected by filtration to give, after being dried under vacuum, 4.9 g. of ethyl 6-acetoxy-5-fluoro-1,2,3,4,5,6-hexahydro-2,4-dioxopyrimidine-5-carboxylate as a white crystalline solid.

m.p. 128°–135° C.

NMR-spectrum (in DMSO-d$_6$) δ: 1.25(3H, t, J=7 Hz), 2.11(3H, s), 4.32(2H, q, J=7 Hz), 6.19(1H, d×d, J=2 Hz and 5.5 Hz), 9.13(1H, broad), 11.33(1H, broad).

This 6-acetoxy compound (2.62 g.) was dissolved in a mixture of 2.5 ml. of acetone and 5 ml. of pyridine. To the solution was added 4.529 g. of cyclohexanone oxime and the solution was heated at 60° C. for one hour. The solvents were evaporated under reduced pressure and the residue was chromatographed on silica gel with chloroform/acetone=87.5/12.5 (V/V) to give 2.65 g. of ethyl 6-cyclohexylideneaminooxy-5-fluoro-1,2,3,4,5,6-hexahydro-2,4-dioxopyrimidine-5-carboxylate.

REFERENCE EXAMPLE 1

In 400 ml. of water was suspended 15.04 g. (80 mmoles) of methyl 1,2,3,4-tetrahydro-2,4-dioxopyrimidine-5-carboxylate monohydrate and the suspension was vigorously stirred at room temperature. Thereafter, a mixed gas of fluorine and nitrogen (1:3, V/V) was passed at a flow rate of about 45 ml./min. for 6.6 hours, with occasional cooling with water to prevent the reaction temperature from rising beyond 28° C. (fluorine consumption: 1.95 molar equivalents.)

While the reaction mixture was cooled, the hydrogen fluoride was neutralized by the addition of 15.6 g. of calcium carbonate, followed by addition of 5.2 g. of sodium hydrogen sulfite. The insolubles were filtered off and the filtrate was concentrated under reduced pressure and dried in vacuo, whereby 23.7 g., powders were obtained.

To the powders was added 500 ml. of acetone, the insolubles were filtered off and the acetone was distilled off under reduced pressure. The residue was subjected to silica gel column chromatography (developing solvent; acetone/chloroform=1/3, V/V). By the above procedure there was obtained 13.0 g. of methyl 5-fluoro-6-hydroxy-1,2,3,4,5,6-hexahydro-2,4-dioxopyrimidine-5-carboxylate.

m.p. 171°–172° C.

NMR spectrum (DMSO-d$_6$) δ: 3.80(3H, s), 4.90(1H, m: after addition of deuterium, d, $J_{HF}$=4Hz), 7.13(1H, d, J=5Hz), 8.53(1H, broad), 10.85(1H, broad).

Elemental analysis, for $C_6H_7FN_2O_5$: Calcd. C, 34.96; H, 3.42; N, 13.59: Found C, 35.07; H, 3.41; N, 13.58.

REFERENCE EXAMPLE 2

In 200 ml. of water was suspended 920 mg. of ethyl 1,2,3,4-tetrahydro-2,4-dioxopyrimidine-5-carboxylate and under intense stirring at room temperature, a mixed gas of fluorine (25 V/V %) and nitrogen was bubbled through the suspension. In due course the starting material dissolved to yield a homogeneous solution.

When 2.6 molar equivalents of said mixed gas had been introduced, the ultraviolet absorption spectrum of the reaction mixture was measured. The reaction was terminated on confirmation of no evidence of unreacted starting material.

The reaction mixture was stirred with 1.10 g. of calcium carbonate for a while, after which the insolubles were filtered off. The filtrate was concentrated to dryness under reduced pressure, whereupon a white solid residue was obtained. This solid product was suspended in 50 ml. of acetone, the insolubles were filtered off and the acetone solution was subjected to silica gel chromatography (developing solvent; chloroform containing 1.5 V/V % of methanol). The fraction rich in the desired compound were concentrated under reduced pressure to obtain a white solid. This was recrystallized from methanol - chloroform - hexane to obtain 561 mg. colorless prisms of ethyl 5-fluoro-6-hydroxy-1,2,3,4,5,6-hexahydro-2,4-dioxopyrimidine-5-carboxylate.

m.p. 163°–165° C.

NMR spectrum (DMSO-d$_6$) δ: 1.22(3H, t, J=7Hz), 4.28(2H, q, J=7Hz), 4.93(1H, d×d, $J_{HF}$=3Hz, J=5Hz; after addition of deuterium, d, $J_{HF}$−3Hz), 6.3(1H, broad), 8.48(1H, broad), 10.80(1H, broad).

Elemental analysis, for $C_7H_9FN_2O_5$: Calcd. C, 38.19; H, 4.12; N, 12.73: Found C, 37.90; H, 3.94; N, 12.87.

REFERENCE EXAMPLE 3

In 200 ml. of acetic acid was dissolved 850 m.g. (5.0 mmoles) of methyl 1,2,3,4-tetrahydro-2,4-dioxopyrimidine-5-carboxylate and at 18°–19° C., a gaseous mixture of 10% fluorine and $N^2$(V/V) was bubbled through the solution. After 23.2 mmoles of fluorine had thus been introduced, the solvent was distilled off under reduced pressure and the residue was dissolved in a mixture of 5 ml. acetone and 20 ml. benzene. The solution was passed through a column of silica gel (10 g.) and elution was carried out with benzene/acetone=4/1 (V/V). The eluate (about 150 ml.) was concentrated to dryness under reduced pressure. By the above procedure there was obtained 1.00 g. of methyl 6-acetoxy-5-fluoro-1,2,3,4,5,6-hexahydro-2,4-dioxopyrimidine-5-carboxylate as a pale-yellow solid.

NMR spectrum (DMSO-d$_6$) δ: 2.08(3H, s), 3.83(3H, s), 6.23 (1H, d×d, J=6Hz & 2Hz); after addition of deuterium, d, J=2Hz), 9.10(1H, broad), 11.33(1H, broad).

We claim:
1. A compound of the formula

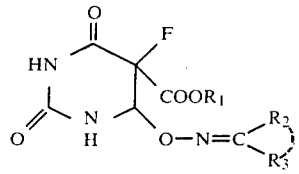

wherein $R_1$ represents a lower alkyl group; and

represents an alkylidene radical in which at least one of $R_2$ and $R_3$ is a lower alkyl group which may be substituted by phenyl, a phenyl group, a furyl group, a thienyl group, or a pyridyl group, no more than one of $R_2$ and $R_3$ being hydrogen; or a cycloalkylidene radical of up to 6 carbon atoms, to which a benzene ring may be fused.

2. A compound according to claim 1 wherein

represents an alkylidene radical in which at least one of $R_2$ and $R_3$ is a lower alkyl, benzyl, phenyl, thienyl, pyridyl or furyl group, no more than one of $R_2$ and $R_3$ being hydrogen; a cycloalkylidene radical having 4 to 6 carbon atoms; or indanylidene.

3. A compound according to claim 2 wherein

represents an alkylidene radical in which at least one of $R_2$ and $R_3$ is a lower alkyl, benzyl, phenyl, thienyl, or furyl group, no more than one of $R_2$ and $R_3$ being hydrogen; cyclobutylidene; cyclopentylidene; cyclohexylidene; or indanylidene.

4. A compound according to claim 2 wherein

represents an alkylidene radical in which at least one of $R_2$ and $R_3$ is a lower alkyl group no more than one of $R_2$ and $R_3$ being hydrogen; or a cycloakylidene radical having 4 to 6 carbon atoms.

5. A compound according to claim 1 which is methyl 5-fluoro-6-cyclohexylideneaminooxy-1,2,3,4,5,6-hexahydro-2,4-dioxopyrimidine-5-carboxylate.

6. A compound according to claim 1 which is ethyl 5-fluoro-6-cyclohexylideneaminooxy-1,2,3,4,5,6-hexahydro-2,4-dioxopyrimidine-5-carboxylate.

7. A compound according to claim 1 which is ethyl 5-fluoro-6-isopropylideneaminooxy-1,2,3,4,5,6-hexahydro-2,4-dioxopyrimidine-5-carboxylate.

8. A compound according to claim 1 which is ethyl 5-fluoro-6-phenylisopropylideneaminooxy-1,2,3,4,5,6-hexahydro-2,4-dioxopyrimidine-5-carboxylate.

9. A compound according to claim 1 which is ethyl 5-fluoro-6-(α,β-diphenyl)ethylideneaminooxy- 1,2,3,4,5,6-hexahydro-2,4-dioxopyrimidine-5-carboxylate.

10. A compound according to claim 1 which is ethyl 5-fluoro-6-(1-indanylidene)aminooxy-1,2,3,4,5,6-hexahydro-2,4-dioxopyrimidine-5-carboxylate.

11. A compound according to claim 1 which is ethyl 5-fluoro-6-(α-2-thienyl)ethylideneaminooxy-1,2,3,4,5,6-hexahydro-2,4-dioxopyrimidine-5-carboxylate.

12. A compound according to claim 1 which is ethyl 5-fluoro-6-(α-4-pyridyl) ethylideneaminooxy-1,2,3,4,5,6-hexahydro-2,4-dioxopyrimidine-5-carboxylate.

13. A compound according to claim 1 which is ethyl 5-fluoro-6-benzylideneaminooxy-1,2,3,4,5,6-hexahydro-2,4-dioxopyrimidine-5-carboxylate.

14. A compound according to claim 1 which is ethyl 5-fluoro-6-isobutylideneaminooxy-1,2,3,4,5,6-hexahydro-2,4-dioxopyrimidine-5-carboxylate.

15. A compound according to claim 1 which is ethyl 5-fluoro-6-(α-methyl)butylideneaminooxy-1,2,3,4,5,6-hexahydro-2,4-dioxopyrimidine-5-carboxylate.

16. A compound according to claim 1 which is ethyl 5-fluoro-6-(α-ethyl)propylideneaminooxy-1,2,3,4,5,6-hexahydro-2,4-dioxopyrimidine-5-carboxylate.

17. A compound according to claim 1 which is ethyl 5-fluoro-6-(α-methyl)pentylideneaminooxy-1,2,3,4,5,6-hexahydro-2,4-dioxopyrimidine-5-carboxylate.

18. A compound according to claim 1 which is ethyl 5-fluoro-6-cyclobutylideneaminooxy-1,2,3,4,5,6-hexahydro-2,4-dioxopyrimidine-5-carboxylate.

19. A compound according to claim 1 which is ethyl 5-fluoro-6-cyclopentylideneaminooxy-1,2,3,4,5,6-hexahydro-2,4-dioxopyrimidine-5-carboxylate.

20. A compound according to claim 1 which is ethyl 5-fluoro-6-[α-(2-furyl)ethylidene]aminooxy-1,2,3,4,5,6-hexahydro-2,4-dioxopyrimidine-5-carboxylate.

21. A compound according to claim 1 which is ethyl 6-ethylideneaminooxy-5-fluoro-1,2,3,4,5,6-hexahydro-2,4-dioxopyrimidine-5-carboxylate.

22. A compound according to claim 1 which is ethyl 5-fluoro-6-α,α-diphenylmethylideneaminooxy-1,2,3,4,5,6-hexahydro-2,4-dioxopyrimidine-5-carboxylate.

23. A compound according to claim 1 which is ethyl 5-fluoro-6-α,α-diisobutylmethylideneaminooxy-1,2,3,4,5,6-hexahydro-2,4-dioxopyrimidine-5-carboxylate.

24. A compound according to claim 1 which is ethyl 5-fluoro-6-(E)-hexylideneaminooxy-1,2,3,4,5,6-hexahydro-2,4-dioxopyrimidine-5-carboxylate.

25. A compound according to claim 1 which is ethyl 5-fluoro-6-(Z)-hexylideneaminooxy-1,2,3,4,5,6-hexahydro-2,4-dioxopyrimidine-5-carboxylate.

26. A pharmaceutical composition for inhibiting the growth of tumerous cells which comprises an effective amount of a compound according to claim 1 and a pharmacologically acceptable carrier.

27. A method for producing a compound of the formula:

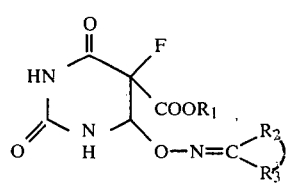

wherein $R_1$ represents a lower alkyl group; and

represents an alkylidene radical in which at least one of $R_2$ and $R_3$ is a lower alkyl which may be substituted by phenyl, a phenyl group, a furyl group, a thienyl group, or a pyridyl group, no more than one of $R_2$ and $R_3$ being hydrogen; or a cycloalkylidene radical of up to six carbon atoms, to which a benzene ring may be fused which comprises reacting a compound of the formula:

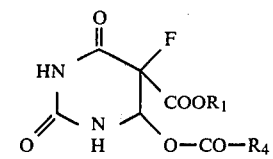

wherein $R_1$ is as defined above and $R_4$—CO— is a carboxylic acid residue, with a compound of the formula:

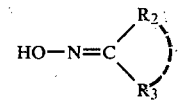

wherein

is as defined above.

28. A method according to claim 27 wherein

represents an alkylidene radical in which at least one of $R_2$ and $R_3$ is a lower alkyl, benzyl, phenyl, thienyl, pyridyl or furyl, no more than one of $R_2$ and $R_3$ being hydrogen; a cycloalkylidene radical having 4 to 6 carbon atoms; or indanylidene.

29. A method for producing a compound of the formula:

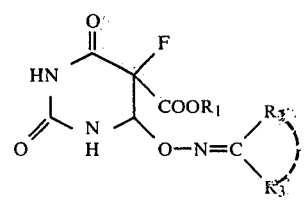

(I)

wherein $R_1$ represents a lower alkyl group; and

represents an alkylidene radical in which at least one of R₂ and R₃ is a lower alkyl which may be substituted by phenyl a phenyl group, a furyl group, a thienyl group, or a pyridyl group, no more than one of R₂ and R₃ being hydrogen; or a cycloalkylidene radical of up to six carbon atoms, to which a benzene ring may be fused which comprises fluorinating a compound of the formula:

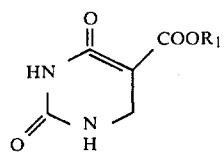 (IV)

wherein $R_1$ is as defined above, in the presence of a carboxylic acid to produce a compound of the formula:

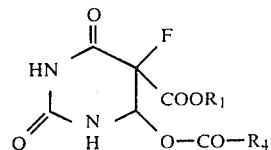 (II)

wherein $R_1$ is as defined above; $R_4$—CO— is a carboxylic acid residue and then reacting the compound of the formula (II) with a compound of the formula:

 (III)

wherein

is defined as above.

* * * * *

UNITED STATES PATENT OFFICE
CERTIFICATE OF CORRECTION

Patent No. 4,190,656        Dated February 26, 1980

Inventor(s) Koichi Matsumura, et al

It is certified that error appears in the above-identified patent and that said Letters Patent are hereby corrected as shown below:

Column 2, line 60, the structural formula (IV) and Column 15, lines 15-20, the structural formula (IV):

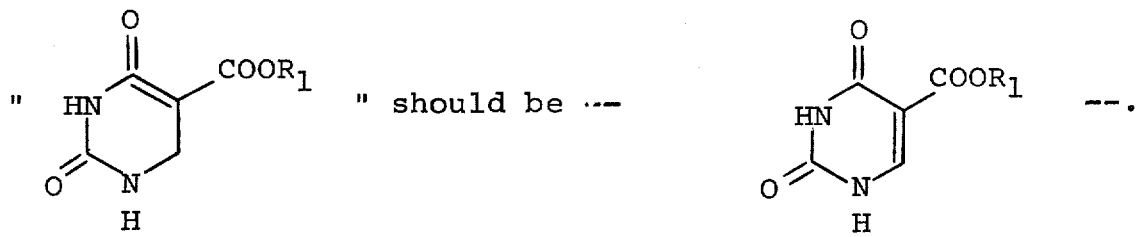

Column 3, line 44:  "our" should be --out--.

Column 4, line 65:  "60" should be --δ:--.

Column 5, line 39:  "H, 4.75;" should be --H, 5.75;--.

Signed and Sealed this

First Day of September 19

[SEAL]

Attest:

GERALD J. MOSSINGHOFF

Attesting Officer    Commissioner of Patents and Trademarks